(12) United States Patent
Hudson et al.

(10) Patent No.: US 10,399,189 B2
(45) Date of Patent: Sep. 3, 2019

(54) AIRFOIL AERODYNAMICS

(71) Applicant: UNITED TECHNOLOGIES CORPORATION, Farmington, CT (US)

(72) Inventors: Eric A. Hudson, Southington, CT (US); Alan C. Barron, Jupiter, FL (US); Edwin Otero, Southington, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 652 days.

(21) Appl. No.: 15/289,801

(22) Filed: Oct. 10, 2016

(65) Prior Publication Data
US 2018/0099362 A1    Apr. 12, 2018

(51) Int. Cl.
*B23P 15/02* (2006.01)
*F01D 5/00* (2006.01)
*F01D 5/14* (2006.01)

(52) U.S. Cl.
CPC .............. *B23P 15/02* (2013.01); *F01D 5/005* (2013.01); *F01D 5/141* (2013.01); *F05D 2220/32* (2013.01); *F05D 2230/10* (2013.01); *Y02T 50/672* (2013.01); *Y02T 50/673* (2013.01); *Y10T 29/49337* (2015.01)

(58) Field of Classification Search
CPC .......... B23P 15/02; F01D 5/005; F01D 5/141; F05D 2230/10; F05D 2220/32; Y10T 29/49337; Y02T 50/673; Y02T 50/672
USPC ........................................................ 29/889.7
See application file for complete search history.

(56) References Cited

U.S. PATENT DOCUMENTS

| | | | |
|---|---|---|---|
| 10,012,976 B2* | 7/2018 | Louesdon | G05B 19/4099 |
| 2002/0091459 A1 | 7/2002 | Meier | |
| 2010/0143704 A1* | 6/2010 | Fujita | B22D 19/14 |
| | | | 428/328 |
| 2013/0298401 A1* | 11/2013 | Sato | B21D 53/78 |
| | | | 29/889.7 |

(Continued)

FOREIGN PATENT DOCUMENTS

EP    0453391    10/1991

OTHER PUBLICATIONS

European Patent Office, European Search Report date Feb. 12, 2018 in Application No. 17193398.9-1006.

(Continued)

*Primary Examiner* — Bayan Salone
(74) *Attorney, Agent, or Firm* — Snell & Wilmer L.L.P.

(57) ABSTRACT

A method of manufacturing an airfoil. The method includes fixing the airfoil in a workpiece space, detecting a position of the airfoil in the workpiece space using a force-sensing element, and removing material from the airfoil to reduce a dimension of the airfoil. In various embodiments, detecting the position of the airfoil includes moving the force-sensing element across a surface of the airfoil. For example, the surface of the airfoil may be a first surface, wherein removing material from the airfoil to reduce the dimension of the airfoil comprises removing material from a second surface of the airfoil opposite the first surface. Removing material from the second surface of the airfoil may be performed without moving the force-sensing element across the second surface of the airfoil.

19 Claims, 8 Drawing Sheets

(56) References Cited

U.S. PATENT DOCUMENTS

2013/0318787 A1* 12/2013 Thomen .................. B23P 15/02
29/889.7
2014/0075754 A1* 3/2014 Barron ................. G05B 19/402
29/888.012
2015/0081074 A1* 3/2015 Louesdon .......... G05B 19/4099
700/98
2015/0361799 A1 12/2015 Rizzo, Jr.

OTHER PUBLICATIONS

Bremer C: Kompressor-Und Turbinenschaufeln Automatisch Reparieren11 , Werkstatt + Betrieb, Carl Hanser Verlag, Munchen DE, vol . 129, No. 7/08, Aug. 1, 1996 (Aug. 1, 1996), pp. 672-674, XP000678763, ISSN: 0043-2792 * p. 672, col. 3-p. 674, col. 1.

* cited by examiner

AIRFOIL AERODYNAMICS

FIELD

The present disclosure relates to gas turbine engines, and more specifically, to airfoil aerodynamics in gas turbine engines.

BACKGROUND

A gas turbine engine typically includes a fan section, a compressor section, a combustor section, and a turbine section. A fan section may drive air along a bypass flowpath while a compressor section may drive air along a core flowpath. In general, during operation, air is pressurized in the compressor section and is mixed with fuel and burned in the combustor section to generate hot combustion gases. The hot combustion gases flow through the turbine section, which extracts energy from the hot combustion gases to power the compressor section and other gas turbine engine loads. The compressor section typically includes low pressure and high pressure compressors, and the turbine section includes low pressure and high pressure turbines.

The fan section, compressor section, and turbine section typically include a series of rotor systems and stator systems. Rotor systems, for example, typically include a disk and a plurality of circumferentially spaced airfoils (e.g., blades). The shape, dimensions, orientation, and configuration of the airfoils contributes to the overall efficiency of a gas turbine engine. For example, a wake of an airfoil is proportional to the thickness of a trailing edge of the airfoil. That is, the thicker the trailing edge of an airfoil is, the more pressure drag the airfoil experiences, thus adversely affecting the operational efficiency of the gas turbine engine. However, reducing the thickness of the trailing edge of airfoils by conventional manufacturing methods may be exorbitantly expensive, labor intensive, and/or time-consuming.

SUMMARY

In various embodiments, the present disclosure provides a method of manufacturing an airfoil of a gas turbine engine. The method may include fixing the airfoil in a workpiece space, detecting a position of the airfoil in the workpiece space using a force-sensing element, and removing material from the airfoil to reduce a dimension of the airfoil. In various embodiments, detecting the position of the airfoil includes moving the force-sensing element across a surface of the airfoil. For example, the surface of the airfoil may be a first surface, wherein removing material from the airfoil to reduce the dimension of the airfoil comprises removing material from a second surface of the airfoil opposite the first surface. Removing material from the second surface of the airfoil may be performed without moving the force-sensing element across the second surface of the airfoil.

In various embodiments, removing material from the second surface of the airfoil is performed substantially simultaneously as moving the force-sensing element across the first surface of the airfoil by using a clamp force-sensing element that has a sensing portion and a cutting portion. In various embodiments, removing material from the airfoil to reduce a thickness of the airfoil comprises utilizing a diamond cutter to cut away material.

Also disclosed herein, according to various embodiments, is another method of manufacturing an airfoil of a gas turbine engine. The method includes fixing the airfoil in a workpiece space, the airfoil having a leading edge, a leading edge portion, a trailing edge, and a trailing edge portion. The method also includes detecting a position of the airfoil in the workpiece space using a force-sensing element, and removing material from at least one of the leading edge portion and the trailing edge portion of the airfoil to reduce a dimension of the one of the leading edge portion and the trailing edge portion.

In various embodiments, detecting the position of the airfoil includes moving the force-sensing element across a surface of the one of the leading edge portion and the trailing edge portion. In various embodiments, surface is a first surface, wherein removing material from the at least one of the leading edge portion and the trailing edge portion of the airfoil includes removing material from a second surface of the one of the leading edge portion and the trailing edge portion of the airfoil, the second surface being opposite the first surface.

In various embodiments, removing material from the second surface is performed without moving the force-sensing element across the second surface of the at least one of the leading edge portion and the trailing edge portion of the airfoil. In various embodiments, the dimension is a thickness of the one of the leading edge portion and the trailing edge portion between the first surface and the second surface. According to various embodiments, removing material from the second surface of the at least one of the leading edge portion and the trailing edge portion of the airfoil includes blending a transition from a pressure side of the airfoil to the second surface.

In various embodiments, removing material from the second surface of the at least one of the leading edge portion and the trailing edge portion of the airfoil includes blending a transition from a suction side of the airfoil to the second surface. Removing material from the at least one of the leading edge portion and the trailing edge portion of the airfoil may include utilizing a diamond cutter to cut away material. The method may include casting the airfoil from raw materials to form the leading edge, the leading edge portion, the trailing edge, and the trailing edge portion. In various embodiments, removing material from at least one of the leading edge portion and the trailing edge portion of the airfoil includes removing body material of the airfoil. In various embodiments, removing material from at least one of the leading edge portion and the trailing edge portion of the airfoil includes removing coating material of the airfoil.

In various embodiments, removing material from the at least one of the leading edge portion and the trailing edge portion of the airfoil includes reducing the dimension by between about 25% and about 75%. In various embodiments, removing material from the one of the leading edge portion and the trailing edge portion of the airfoil is performed while the airfoil is uncooled.

Also disclosed herein, according to various embodiments, is another method of manufacturing an airfoil of a gas turbine engine. The method includes fixing the airfoil in a workpiece space, the airfoil having a leading edge, a leading edge portion, a trailing edge, a trailing edge portion, a suction side, and a pressure side. The method also includes detecting a position of the airfoil in the workpiece space by moving a force-sensing element across a first surface of one of the leading edge portion and the trailing edge portion of the airfoil. Further, the method includes removing material from a second surface, opposite the first surface, of the one of the leading edge portion and the trailing edge portion of the airfoil to reduce a dimension of the one of the leading edge portion and the trailing edge portion of the airfoil and to blend a transition from one of the pressure side and the suction side of the airfoil to the second surface.

The forgoing features and elements may be combined in various combinations without exclusivity, unless expressly indicated herein otherwise. These features and elements as well as the operation of the disclosed embodiments will become more apparent in light of the following description and accompanying drawings.

Figure 1:
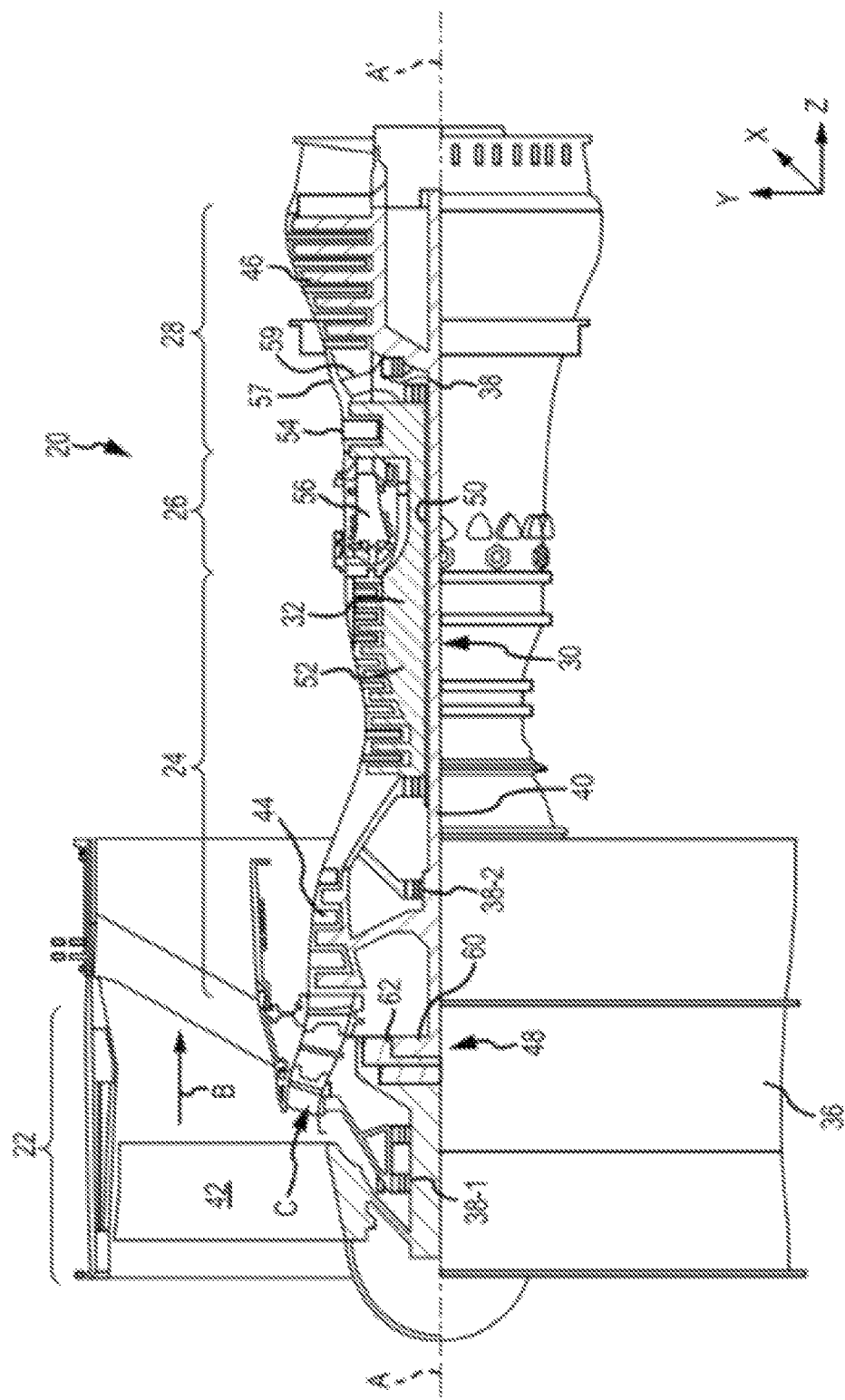
FIG. 1 illustrates a cross-sectional view of an exemplary gas turbine engine, in accordance with various embodiments.

The subject matter of the present disclosure is particularly pointed out and distinctly claimed in the concluding portion of the specification. A more complete understanding of the present disclosure, however, may best be obtained by referring to the detailed description and claims when considered in connection with the drawing figures, wherein like numerals denote like elements.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the disclosure, it should be understood that other embodiments may be realized and that logical changes and adaptations in design and construction may be made in accordance with this disclosure and the teachings herein without departing from the spirit and scope of the disclosure. Thus, the detailed description herein is presented for purposes of illustration only and not of limitation.

In various embodiments and with reference to FIG. 1, a gas turbine engine 20 is provided. Gas turbine engine 20 may be a two-spool turbofan that generally incorporates a fan section 22, a compressor section 24, a combustor section 26 and a turbine section 28. Alternative engines may include, for example, an augmentor section among other systems or features. In operation, fan section 22 can drive coolant (e.g., air) along a bypass flow-path B while compressor section 24 can drive coolant along a core flow-path C for compression and communication into combustor section 26 then expansion through turbine section 28. Although depicted as a turbofan gas turbine engine 20 herein, it should be understood that the concepts described herein are not limited to use with turbofans as the teachings may be applied to other types of turbine engines including three-spool architectures.

Gas turbine engine 20 may generally comprise a low speed spool 30 and a high speed spool 32 mounted for rotation about an engine central longitudinal axis A-A' relative to an engine static structure 36 or engine case via several bearing systems 38, 38-1, and 38-2. Engine central longitudinal axis A-A' is oriented in the z direction on the provided xyz axis. It should be understood that various bearing systems 38 at various locations may alternatively or additionally be provided, including for example, bearing system 38, bearing system 38-1, and bearing system 38-2.

Low speed spool 30 may generally comprise an inner shaft 40 that interconnects a fan 42, a low pressure compressor 44 and a low pressure turbine 46. Inner shaft 40 may be connected to fan 42 through a geared architecture 48 that can drive fan 42 at a lower speed than low speed spool 30. Geared architecture 48 may comprise a gear assembly 60 enclosed within a gear housing 62. Gear assembly 60 couples inner shaft 40 to a rotating fan structure. High speed spool 32 may comprise an outer shaft 50 that interconnects a high pressure compressor 52 and high pressure turbine 54. A combustor 56 may be located between high pressure compressor 52 and high pressure turbine 54. A mid-turbine frame 57 of engine static structure 36 may be located generally between high pressure turbine 54 and low pressure turbine 46. Mid-turbine frame 57 may support one or more bearing systems 38 in turbine section 28. Inner shaft 40 and outer shaft 50 may be concentric and rotate via bearing systems 38 about the engine central longitudinal axis A-A', which is collinear with their longitudinal axes. As used herein, a "high pressure" compressor or turbine experiences a higher pressure than a corresponding "low pressure" compressor or turbine.

The core airflow C may be compressed by low pressure compressor 44 then high pressure compressor 52, mixed and burned with fuel in combustor 56, then expanded over high pressure turbine 54 and low pressure turbine 46. Turbines 46, 54 rotationally drive the respective low speed spool 30 and high speed spool 32 in response to the expansion.

In various embodiments, geared architecture 48 may be an epicyclic gear train, such as a star gear system (sun gear in meshing engagement with a plurality of star gears supported by a carrier and in meshing engagement with a ring gear) or other gear system. Geared architecture 48 may have a gear reduction ratio of greater than about 2.3 and low pressure turbine 46 may have a pressure ratio that is greater than about five (5). In various embodiments, the bypass ratio of gas turbine engine 20 is greater than about ten (10:1). In various embodiments, the diameter of fan 42 may be significantly larger than that of the low pressure compressor 44, and the low pressure turbine 46 may have a pressure ratio that is greater than about five (5:1). Low pressure turbine 46 pressure ratio may be measured prior to inlet of low pressure turbine 46 as related to the pressure at the outlet of low pressure turbine 46 prior to an exhaust nozzle. It should be understood, however, that the above parameters are exemplary of various embodiments of a suitable geared architecture engine and that the present disclosure contemplates other gas turbine engines including direct drive turbofans. A gas turbine engine may comprise an industrial gas turbine (IGT) or a geared aircraft engine, such as a geared turbofan, or non-geared aircraft engine, such as a turbofan, or may comprise any gas turbine engine as desired.

The fan section 22, the compressor section 24 and the turbine section 28 may each comprise rotor systems including blade assemblies having one or more sets of rotating blades, which may rotate about engine central longitudinal axis A-A'. In a gas turbine engine, improving the aerodynamics of flowpath components, such as airfoils, generally leads to more efficient engine performance. Streamlining the shape and dimensions of flowpath components, such as airfoils, decreases the size of the wake downstream of the flowpath components and thus decreases the pressure drag experienced by such components, thereby requiring less energy expenditure for moving internal engine parts.

In various embodiments, an airfoil is disclosed herein. The term "airfoil" refers to rotor components and stator components that are present in the flowpath(s) of the gas turbine engine 20. That is, in various embodiments the term "airfoil" may refer to rotors such as fan blades, compressor blades, and/or turbine blades. In various embodiments, the term "airfoil" may refer to stators such as fan vanes, compressor vanes, and/or turbine vanes. Accordingly, while numerous details and depictions included herein may be in reference to rotors and/or blades, the scope of the present disclosure is not limited to rotor blades and thus the subject matter of the present disclosure may be applicable to a variety of airfoil flowpath components, both stators and rotors.

Figure 2A:
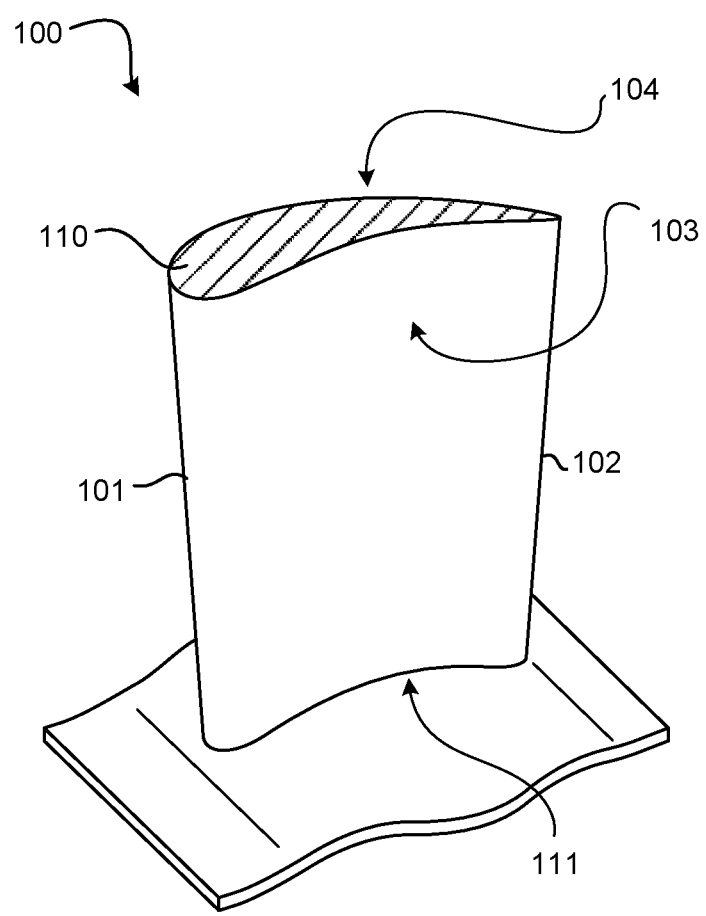
FIG. 2A illustrates a perspective cross-sectional view of an airfoil, in accordance with various embodiments.

With reference to FIG. 2A, an airfoil 100 having a body 110 is disclosed. The airfoil 100 may include a hub end 111 for attaching the airfoil 100 to a hub of, for example, a rotor system. The airfoil 100 may also have a radially outer edge or tip located radially outward from the hub end 111. The airfoil 100 may have a leading edge 101 opposite a trailing edge 102. In various embodiments, the airfoil 100 may further include a generally concave pressure surface 103 and a generally convex suction 104 surface joined together at the respective leading edge 101 and trailing edge 102. The airfoil 100 may be curved and twisted relative to, for example, a plane extending radially from the disk, in terms of the overall geometry of the airfoil 100.

It will be noted that airfoils for gas turbine engines may be provided in a variety of sizes, shapes and geometries. Accordingly, the airfoil 100 of the present disclosure is not limited to the specific geometry, size, and shape shown in the figures. Further, as mentioned above, the disclosed airfoil 100 is not necessarily limited to the turbine section 28 of a gas turbine engine 20, but instead may be implemented in other sections of the gas turbine engine 20 and/or may be adapted for use in other types of jet engines, propellers, rotors, stators, etc.

In various embodiments, the body 110 of the airfoil 100 may be fabricated from a metallic material, such as a metal and/or a metal alloy. In various embodiments, for example, the body 110 of the airfoil 100 may be fabricated from aluminum, an aluminum alloy, titanium, a titanium alloy, and/or a nickel chromium alloy, monolithic ceramic, or ceramic matrix composites, among other suitable materials.

As mentioned above, the aerodynamics of the airfoil 100 may contribute to the efficiency of the gas turbine engine 20. Accordingly, manufacturing the airfoil 100 to have desired a shape and desired dimensions may improve operation of the gas turbine engine 20. In various embodiments, and with reference to FIG. 6, the dimension, shape, and thickness of a leading edge portion 106 (a section of the airfoil 100 proximate the leading edge 101) and a trailing edge portion 107 (a section of the airfoil 100 proximate the trailing edge 102) may be particularly influential on the overall aerodynamic performance of the airfoil 100. For example, the thickness of the trailing edge portion 107 of the airfoil 100 is generally proportional to the size of the wake located downstream of the trailing edge 102 and thus contributes to the magnitude of the pressure drag experienced by the airfoil 100. Additionally, the shape and/or geometry of the trailing edge portion 107 as it transitions/tapers to the trailing edge 102 also contributes to the magnitude of the pressure drag exerted on the airfoil 100. For example, if a trailing edge portion has an abrupt transition to the trailing edge or if the trailing edge were blunt, the fluid (e.g., air, gas) flowing around the airfoil would separate from the surface of the airfoil, creating a low-pressure region (i.e., a "wake") that would create pressure drag.

Figure 2B:
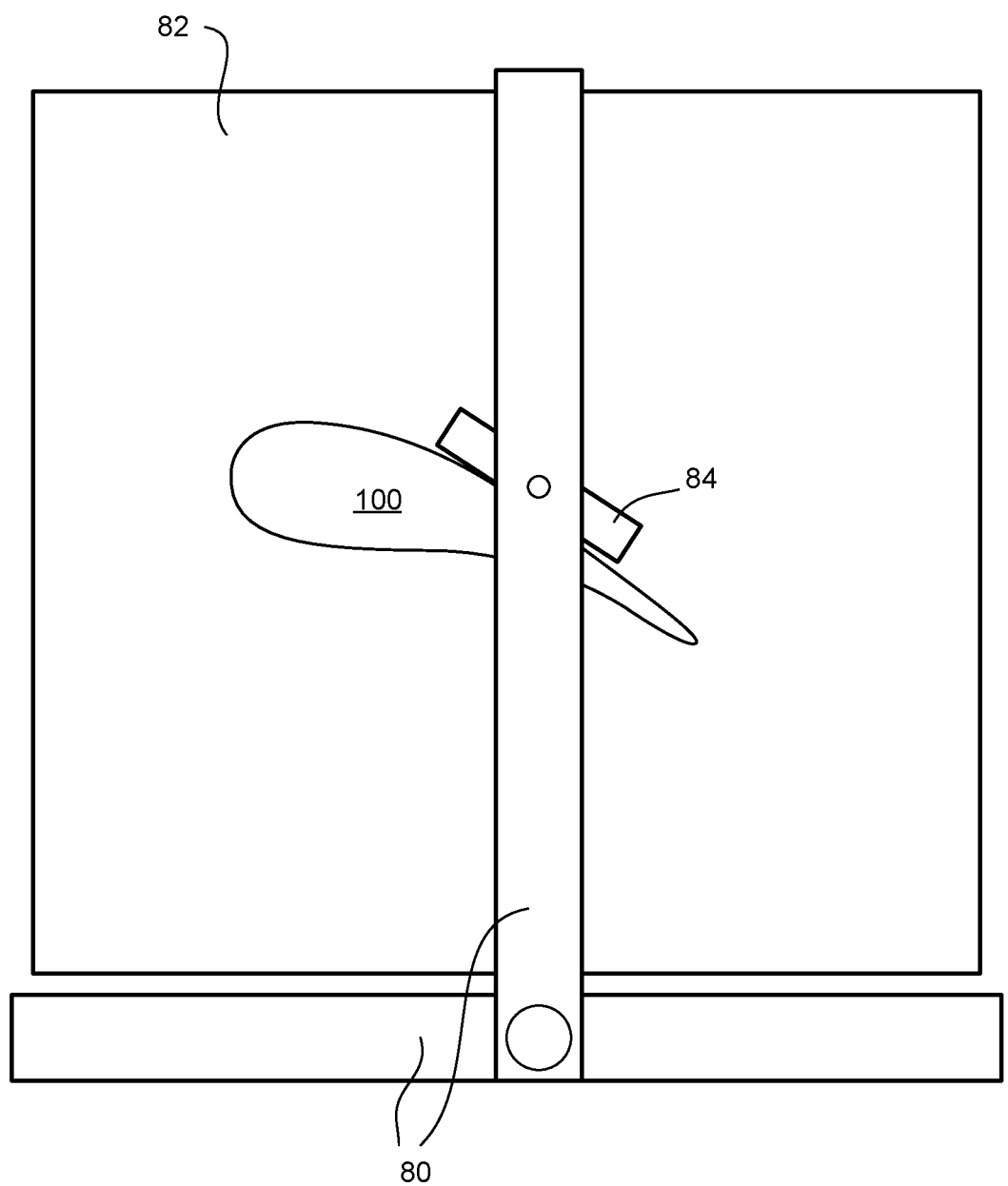
FIG. 2B illustrates a schematic view of an airfoil fixed within a workpiece space of a robotic assembly, in accordance with various embodiments.
Figure 3:
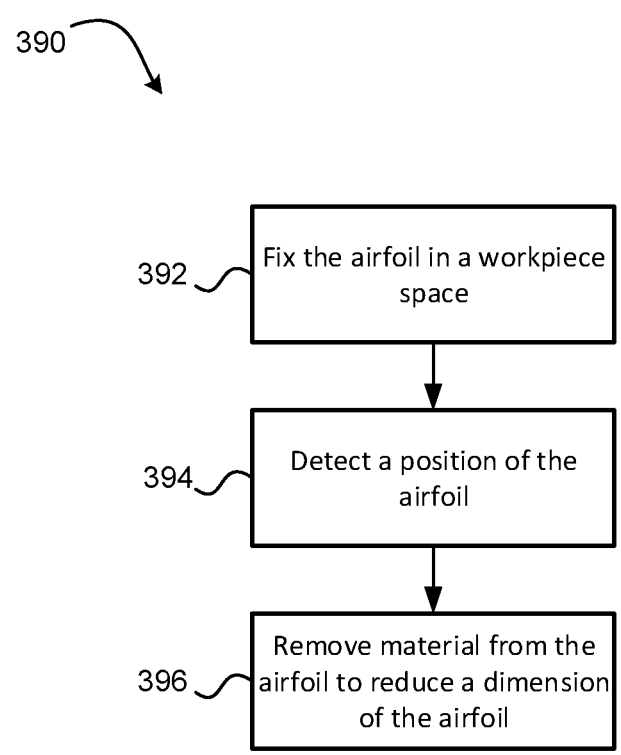
FIG. 3 is a schematic flowchart diagram of a method of manufacturing an airfoil, in accordance with various embodiments.

In various embodiments, and with reference to FIGS. 2B and 3, the present disclosure provides a method 390 for manufacturing the airfoil 100 to improve its aerodynamic properties. The method 390 includes steps for streamlining the shape and geometry of the airfoil 100 after it has been cast, according to various embodiments. As mentioned above, due to cost, labor, and/or time constraints, it may be impractical, using conventional methods, to cast or otherwise form an airfoil having the desired geometry and dimensions. It may also be impractical, using conventional methods, to improve the aerodynamic properties of a conventional airfoil.

The method 390 includes, according to various embodiments, fixing the airfoil 100 in a workpiece space 82 (step 392). The workpiece space 82 is defined herein as the working area of a robotic assembly 80. That is, the airfoil is mounted in a fixed manner in workable proximity to a robotic assembly 80 or other computer controlled machining assembly. The method 390, according to various embodiments, further includes detecting the position of the airfoil 100 in the workpiece space 82 using a force-sensing element 84 (step 394). In various embodiments, step 394 includes utilizing a force-sensing element 84 attached to a robotic assembly 80 that perceives the airfoil to determine the relative position of the airfoil 100 with respect to the robotic assembly 80 (e.g., with respect to the workable volume/space of the robotic 80 assembly).

With the relative position of the airfoil 100 known, the method 390 further includes, according to various embodiments, removing material from the airfoil 100 to reduce a dimension of the airfoil 100 (step 396). In various embodiments, step 396 includes utilizing a cutting, milling, plasma, or laser tool, among others, that is attached to the same robotic assembly 80 (or at least a robotic assembly that has access to the detected relative position of the airfoil 100 and is calibrated to the workpiece space 82) to remove material from the airfoil 100. In various embodiments, step 396 may include utilizing a diamond cutting device to remove material from the airfoil 100. In various embodiments, the material removed may be material from the body 110 of the airfoil 100 and/or the material removed may be a coating material that was applied over the surface(s) of the airfoil 100.

In various embodiments, step 394 includes moving the force-sensing element 84 across a first surface of the airfoil 100, thereby determining a geometry and the position of the first surface of the airfoil 100. Accordingly, step 396, according to various embodiments, may include removing material from a second surface of the airfoil 100, the second surface being different than the first surface. In various embodiments, as described in greater detail below, the second surface may be opposite (e.g., a suction side is opposite a pressure side of an airfoil) the first surface. That is, according to various embodiments, the step of removing material from the airfoil (step 396) may include removing material from a surface of the airfoil that has not been perceived (e.g., touched/engaged) by the force-sensing element 84 during step 394.

In various embodiments, the steps of determining the position of the airfoil 100 (step 394) and removing material from the airfoil (step 396) may be performed substantially simultaneously. In various embodiments, for example, the force-sensing element 84 may have a clamping structure that includes a sensing portion and a cutting portion. The cutting portion of the clamping structure of the force-sensing element 84 may remove material from the second surface of the airfoil 100 as the sensing portion of clamping structure of the force-sensing element 84 moves along and follows the first surface of the airfoil.

Figure 4:
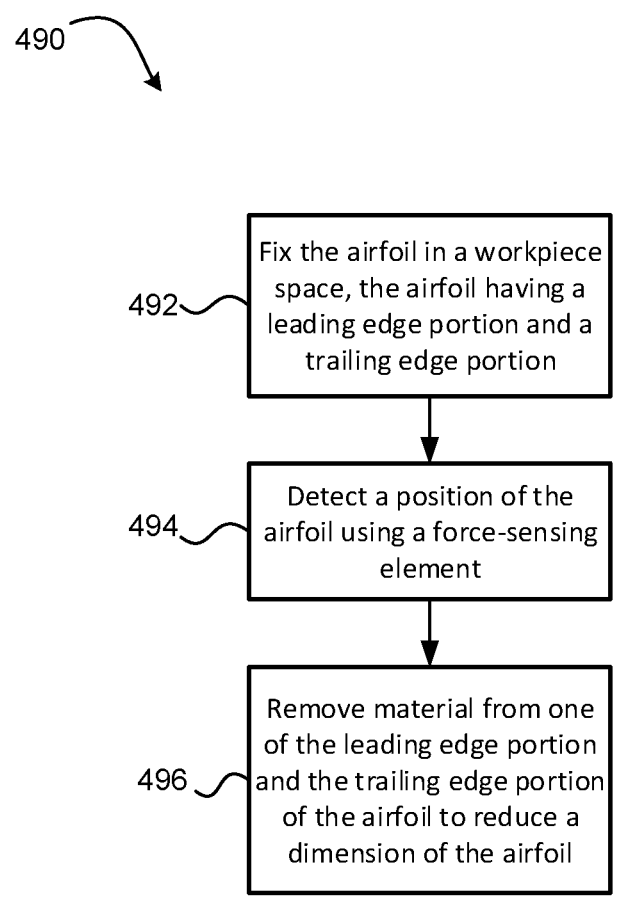
FIG. 4 is a schematic flowchart diagram of another method of manufacturing an airfoil, in accordance with various embodiments.
Figure 6:
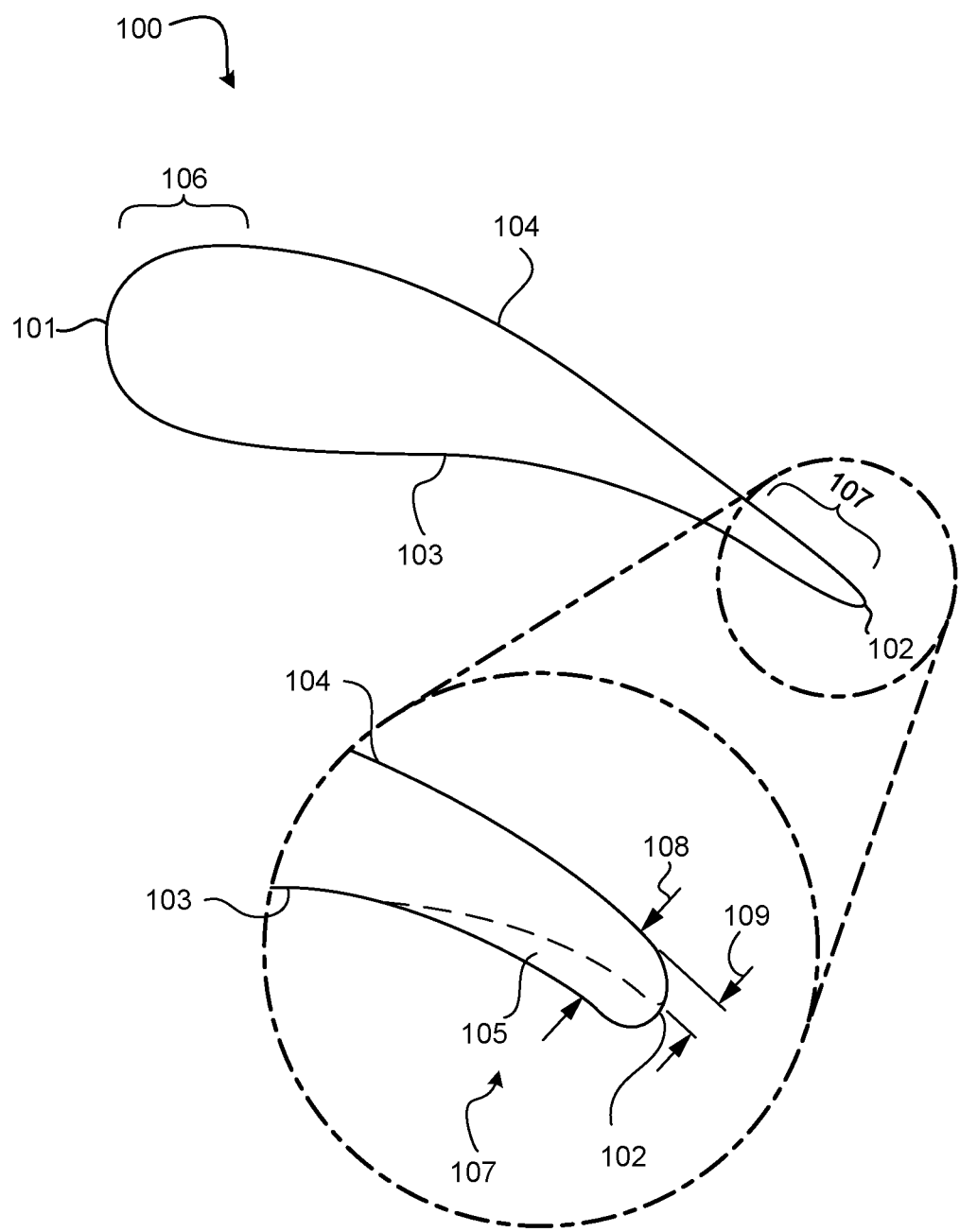
FIG. 6 illustrates a cross-sectional view, including a magnified cross-sectional view, of an airfoil, in accordance with various embodiments.
Figure 7:
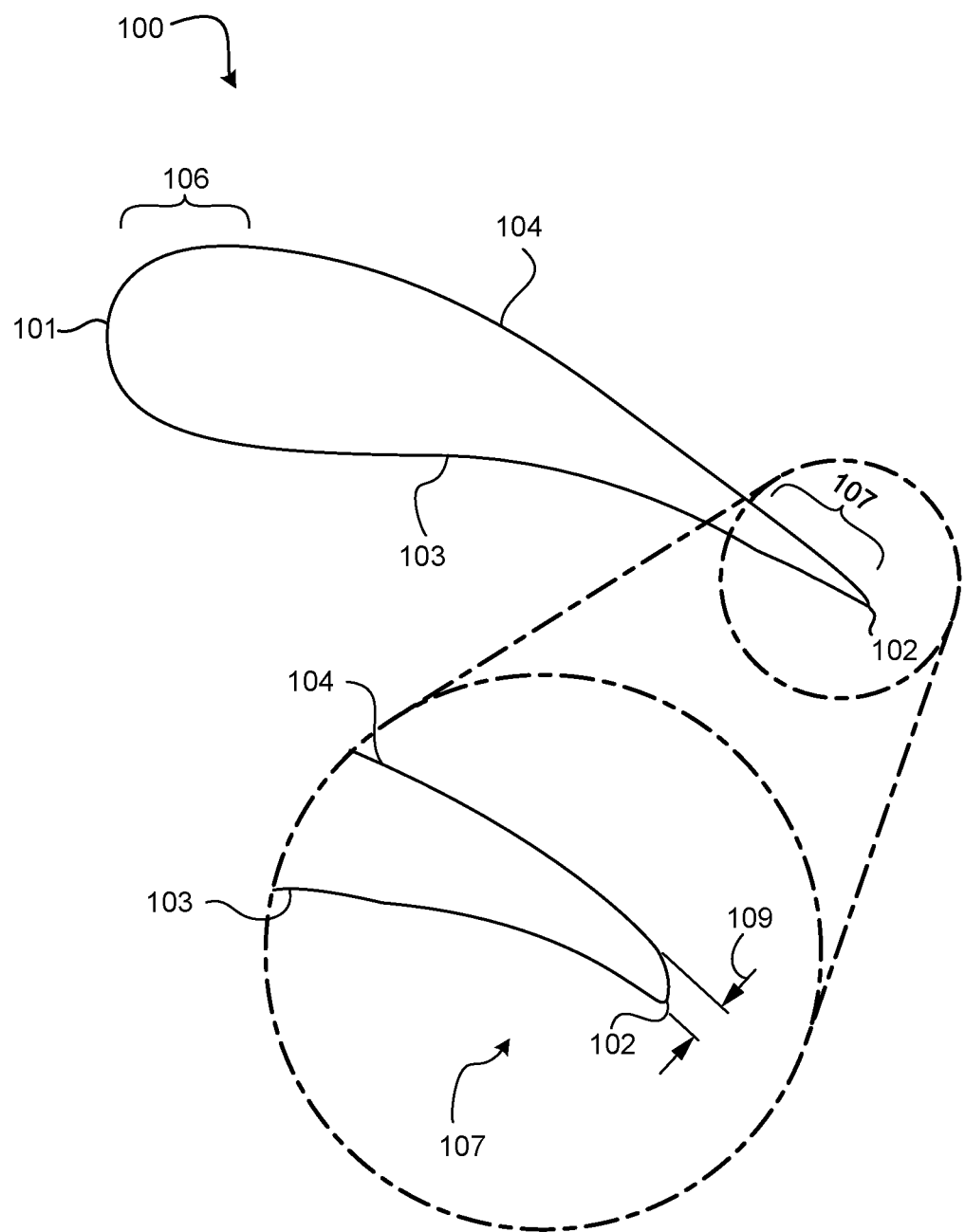
FIG. 7 illustrates a cross-sectional view, including a magnified cross-sectional view, of an airfoil, in accordance with various embodiments.

Disclosed herein with reference to FIG. 4 in conjunction with FIGS. 6 and 7 is another method 490 of manufacturing the airfoil 100, according to various embodiments. The method 490 includes steps 492, 494, 496 that are similar to the like numbered steps described above with reference to FIG. 3. Accordingly, the method 490 includes fixing the airfoil 100 in the workpiece space 82. The airfoil 100, with reference to FIG. 6, includes a leading edge 101, a leading edge portion 106, a trailing edge 102, and a trailing edge portion 107, according to various embodiments. As briefly described above, the leading edge portion 106 is the section of the airfoil 100 that is in proximity to and/or that immediately surrounds the leading edge 101 of the airfoil 100 and the trailing edge portion 107 is the section of the airfoil 100 that is in proximity to and/or that immediately surrounds the trailing edge 102 of the airfoil.

The method 490 further includes, according to various embodiments, detecting the position of the airfoil in the workpiece space 82 using the force-sensing element 84 (step 494). This detecting step 494 may include moving the force-sensing element 84, via an automated scan managed by the robotic assembly 80, across a surface of the either the leading edge portion 106 or the trailing edge portion 107, according to various embodiments. That is, in various embodiments, the surface across which the force-sensing element 84 moves to determine the position of the airfoil may be the leading edge portion 106 of the pressure side 103 of the airfoil 100, the leading edge portion 106 of the suction side 104 of the airfoil 100, the trailing edge portion 107 of the pressure side 103 of the airfoil 100, or the trailing edge portion 107 of the suction side 104 of the airfoil 100. In various embodiments, step 494 may include moving the force-sensing element 84 across a plurality of the above mentioned surfaces.

The method 490 may further include removing material from the leading edge portion 106 (the pressure side 103, the suction side 104, or both) and/or the trailing edge portion 107 (the pressure side 103, the suction side 104, or both) to reduce a dimension of the airfoil 100. In various embodiments, and with reference to FIG. 6, the trailing edge portion 107 of the airfoil 100 is shown with a material to be removed 105. That is, step 496 of the method 490 may include utilizing a cutting tool that is attached to and moved by a robotic assembly 80 to cut away at the pressure side 103 of the trailing edge portion 107 to remove material 105, thereby changing the dimension of the trailing edge portion 107 from a first thickness 108 to a second thickness 109 that is less than the first thickness 108. FIG. 7 illustrates how the trailing edge portion 107 of the airfoil 100 looks after removal of the material 105 via step 496.

The amount of material removed 105 and the relative size, orientation, geometry, and shape of the trailing edge portion 107 of the airfoil 100 shown in FIGS. 6 and 7 is exaggerated, according to various embodiments, in order to clearly depict the results of the method 490. Thus, the scope of the present disclosure is not to be limited by the relative size of the features shown/depicted in the figures. In various embodiments, step 496 of the method 490 includes reducing the dimension of the airfoil by between about 25% and about 75%. For example, the first thickness 108 (i.e., pre-removal step) of the trailing edge portion 107 of the airfoil 100 may be about 0.020 inches (0.051 centimeters) and the second thickness 109 (i.e., post-removal step) of the airfoil 100 may be between about 0.015 inches (0.038 centimeters) and about 0.005 inches (0.013 centimeters). In various embodiments, step 496 of the method 490 includes reducing the dimension of the airfoil by about 50%. For example, the first thickness 108 (i.e., pre-removal step) of the trailing edge portion 107 of the airfoil 100 may be about 0.020 inches (0.051 centimeters) and the second thickness 109 (i.e., post-removal step) of the airfoil 100 may be about 0.010 inches (0.025 centimeters).

In various embodiments, the step 496 of the method 490 may include, in addition to removing material (e.g., material 105) from the leading edge portion 106 or the trailing edge portion 107 (or both), blending the leading edge portion 106 and/or the trailing edge portion 107 to transition to the geometry of the pressure side 103 or the suction side 104 of the airfoil. That is, in various embodiments the step 496 of the method 490 includes smoothing a transition between the leading edge portion 106 and/or the trailing edge portion 107 to the pressure side 103 of the suction side 104 of the airfoil 100. In various embodiments, the method 490, or at least step 496 of the method 490, may be performed when the trailing edge portion of the airfoil is uncooled. In various embodiments, the airfoil 100 may be internally convectively cooled and/or may have film holes upstream of the trailing edge 102 (e.g., in the trailing edge portion 107) of the airfoil 100.

Figure 5:
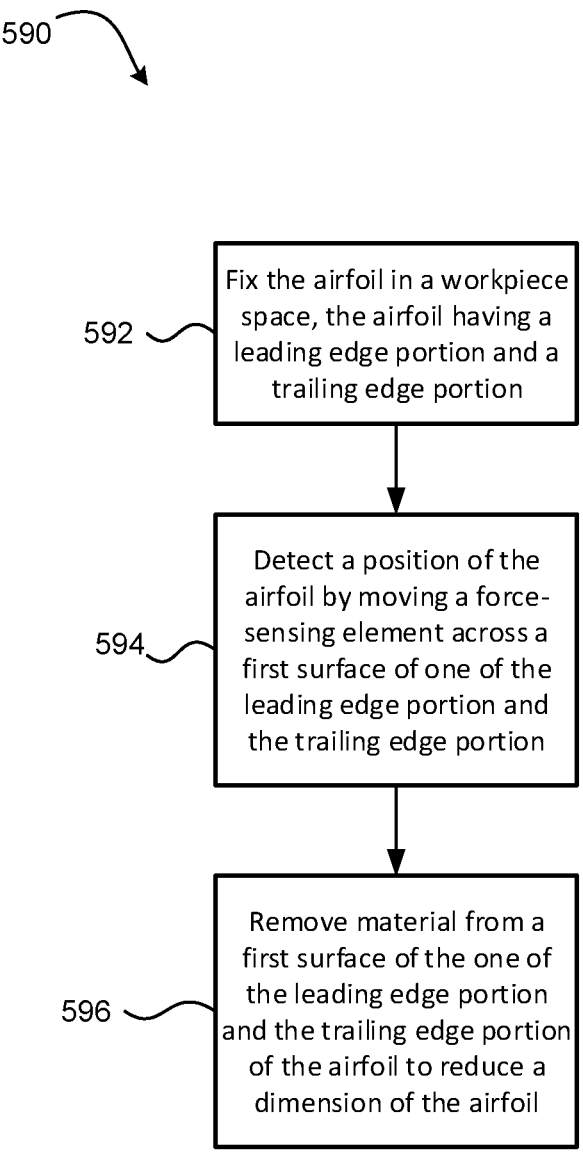
FIG. 5 is a schematic flowchart diagram of yet another method of manufacturing an airfoil, in accordance with various embodiments.

In various embodiments, and with reference to FIG. 5, another method 590 for manufacturing the airfoil 100 is disclosed. The method 590 includes, according to various embodiments, fixing the airfoil in a workpiece space 82, the airfoil having a leading edge, a leading edge portion, a trailing edge, a trailing edge portion, a suction side, and a pressure side (step 592). The method 590 may further include detecting a position of the airfoil in the workpiece space 82 by moving a force-sensing element 84 across a first surface of one of the leading edge portion and the trailing edge portion of the airfoil (step 594). The method 590 may also include removing material from a second surface, opposite the first surface, of the one of the leading edge portion and the trailing edge portion of the airfoil to reduce a dimension of the one of the leading edge portion and the trailing edge portion of the airfoil and to blend a transition from one of the pressure side and the suction side of the airfoil to the second surface (step 596).

As used herein, "aft" refers to the direction associated with the exhaust (e.g., the back end) of a gas turbine engine. As used herein, "forward" refers to the direction associated with the intake (e.g., the front end) of a gas turbine engine.

A first component that is "axially outward" of a second component means that a first component is positioned at a greater distance in the aft or forward direction away from the longitudinal center of the gas turbine along the longitudinal axis of the gas turbine, than the second component. A first component that is "axially inward" of a second component means that the first component is positioned closer to the longitudinal center of the gas turbine along the longitudinal axis of the gas turbine, than the second component.

A first component that is "radially outward" of a second component means that the first component is positioned at a greater distance away from the engine central longitudinal axis than the second component. A first component that is "radially inward" of a second component means that the first component is positioned closer to the engine central longitudinal axis than the second component. In the case of components that rotate circumferentially about the engine central longitudinal axis, a first component that is radially inward of a second component rotates through a circumferentially shorter path than the second component. The terminology "radially outward" and "radially inward" may also be used relative to references other than the engine central longitudinal axis. For example, a first component of a combustor that is radially inward or radially outward of a second component of a combustor is positioned relative to the central longitudinal axis of the combustor.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, and C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

The steps recited in any of the method or process descriptions may be executed in any order and are not necessarily limited to the order presented. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods and apparatus are provided herein. In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method of manufacturing an airfoil of a gas turbine engine, the method comprising:
    fixing the airfoil in a workpiece space;
    detecting a position of the airfoil in the workpiece space using a force-sensing element; and
    removing material from the airfoil to reduce a dimension of the airfoil;
    wherein removing material from the airfoil is performed substantially simultaneously as detecting the position of the airfoil in the workpiece space.

2. The method of claim 1, wherein detecting the position of the airfoil comprises moving the force-sensing element across a surface of the airfoil.

3. The method of claim 2, wherein the surface of the airfoil is a first surface, wherein removing material from the airfoil to reduce the dimension of the airfoil comprises removing material from a second surface of the airfoil opposite the first surface.

4. The method of claim 3, wherein removing material from the second surface of the airfoil is performed without moving the force-sensing element across the second surface of the airfoil.

5. The method of claim 3, wherein removing material from the second surface of the airfoil is performed substantially simultaneously as moving the force-sensing element across the first surface of the airfoil by using a clamp force-sensing element having a sensing portion and a cutting portion.

6. The method of claim 1, wherein removing material from the airfoil to reduce a thickness of the airfoil comprises utilizing a diamond cutter to cut away material.

7. A method of manufacturing an airfoil of a gas turbine engine, the method comprising:

fixing the airfoil in a workpiece space, the airfoil having a leading edge, a leading edge portion, a trailing edge, and a trailing edge portion;

detecting a position of the airfoil in the workpiece space using a force-sensing element; and removing material from at least one of the leading edge portion and the trailing edge portion of the airfoil to reduce a dimension of the one of the leading edge portion and the trailing edge portion, wherein removing material from the one of the leading edge portion and the trailing edge portion of the airfoil is performed while the trailing edge portion of the airfoil is uncooled.

8. The method of claim 7, wherein detecting the position of the airfoil comprises moving the force-sensing element across a surface of the one of the leading edge portion and the trailing edge portion.

9. The method of claim 8, wherein the surface is a first surface, wherein removing material from the at least one of the leading edge portion and the trailing edge portion of the airfoil comprises removing material from a second surface of the one of the leading edge portion and the trailing edge portion of the airfoil, the second surface being opposite the first surface.

10. The method of claim 9, wherein removing material from the second surface is performed without moving the force-sensing element across the second surface of the at least one of the leading edge portion and the trailing edge portion of the airfoil.

11. The method of claim 9, wherein the dimension is a thickness of the one of the leading edge portion and the trailing edge portion between the first surface and the second surface.

12. The method of claim 9, wherein removing material from the second surface of the at least one of the leading edge portion and the trailing edge portion of the airfoil comprises blending a transition from a pressure side of the airfoil to the second surface.

13. The method of claim 9, wherein removing material from the second surface of the at least one of the leading edge portion and the trailing edge portion of the airfoil comprises blending a transition from a suction side of the airfoil to the second surface.

14. The method of claim 7, wherein removing material from the at least one of the leading edge portion and the trailing edge portion of the airfoil comprises utilizing a diamond cutter to cut away material.

15. The method of claim 7, further comprising casting the airfoil from raw materials to form the leading edge, the leading edge portion, the trailing edge, and the trailing edge portion.

16. The method of claim 7, wherein removing material from at least one of the leading edge portion and the trailing edge portion of the airfoil comprises removing body material of the airfoil.

17. The method of claim 7, wherein removing material from at least one of the leading edge portion and the trailing edge portion of the airfoil comprises removing coating material of the airfoil.

18. The method of claim 7, wherein removing material from the at least one of the leading edge portion and the trailing edge portion of the airfoil comprises reducing the dimension by between about 25% and about 75%.

19. A method of manufacturing an airfoil of a gas turbine engine, the method comprising:

fixing the airfoil in a workpiece space, the airfoil having a leading edge, a leading edge portion, a trailing edge, a trailing edge portion, a suction side, and a pressure side;

detecting a position of the airfoil in the workpiece space by moving a force-sensing element across a first surface of one of the leading edge portion and the trailing edge portion of the airfoil; and removing material from a second surface, opposite the first surface, of the one of the leading edge portion and the trailing edge portion of the airfoil to reduce a dimension of the one of the leading edge portion and the trailing edge portion of the airfoil, wherein removing material from the second surface of the airfoil is performed substantially simultaneously as moving the force-sensing element across the first surface of the airfoil by using a clamp force-sensing element having a sensing portion and a cutting portion.

* * * * *